United States Patent [19]

Synodis et al.

[11] Patent Number: 6,017,520
[45] Date of Patent: Jan. 25, 2000

[54] PENETRATION ENHANCEMENT OF TOPICALLY APPLIED THERAPEUTIC FORMULATIONS

[75] Inventors: Joseph Synodis, Summit, N.J.; Stuart Wilensky, Brooklyn, N.Y.

[73] Assignee: Block Drug Company, Inc., Jersey City, N.J.

[21] Appl. No.: 08/850,377

[22] Filed: May 2, 1997

Related U.S. Application Data

[62] Division of application No. 07/785,426, Oct. 23, 1991, abandoned.

[51] Int. Cl.⁷ .............................. A61K 9/107; A61K 9/70
[52] U.S. Cl. ....................... 424/78.02; 424/443; 424/433; 424/436; 424/78.03; 424/70.1; 424/78.05; 514/937; 514/944; 514/945; 514/947
[58] Field of Search ..................... 424/436, 443, 424/433, 78.03, 78.05, 70.1, 78.02; 514/937, 944, 945, 947

[56] References Cited

U.S. PATENT DOCUMENTS

| | | | |
|---|---|---|---|
| 4,177,267 | 12/1979 | Herschler | 424/70.1 |
| 4,808,414 | 2/1989 | Peck | 424/449 |
| 4,824,676 | 4/1989 | Bodor | 424/443 |
| 4,847,069 | 7/1989 | Bissett | 424/64 |
| 4,869,897 | 9/1989 | Chatlesjee | 424/70 |
| 4,886,783 | 12/1989 | Minashanian | 514/179 |
| 4,917,896 | 4/1990 | Peck | 424/449 |
| 4,948,588 | 8/1990 | Kamija | 424/443 |
| 5,015,470 | 5/1991 | Gibson | 424/70.11 |
| 5,032,403 | 7/1991 | Sinnreich | 424/443 |
| 5,215,759 | 6/1993 | Mausner | 424/489 |
| 5,482,965 | 1/1996 | Rajadhyaksha | 514/452 |

FOREIGN PATENT DOCUMENTS

| | | |
|---|---|---|
| 1257200 | 7/1989 | Canada . |
| 2601489 | 2/1990 | Germany . |
| 01-283208 | 11/1989 | Japan . |

OTHER PUBLICATIONS

Database WPIL, Derwent Publications Ltd., AN 89–375632 & JP–A–1 283 208.
Database WPIL, Derwent Publications Ltd., AN 80–54158C & JP–A–55 079 318.
Database WPIL, Derwent Publications Ltd., AN 83–45392K & JP–A–58 055 417.
Database WPIL, Derwent Publications Ltd., AN 81–24647D & JP–A–56010 887.
"Uptake Storage and Excretion of Chylomicra–Bound $^3$H–α–Tocopherol by the Skin of the Rat"; Tatsuji Shiratori; Life Sciences; vol. 14; pp. 929–935; 1974.
"Improvement of Cyclosporin Absorption in Children after Liver Transplantation by Means of Water–Soluble Vitamin E"; Ronald J. Sokol, et al.; *The Lancet*; vol. 338; Jul. 27, 1991.

*Primary Examiner*—Raj Bawa

[57] ABSTRACT

Described is the use of vitamin E in topically applied compositions for the purpose of enhancing the penetration of therapeutically effective (cosmetically or pharmaceutically-active) drug or cosmetic ingredients. The topical compositions containing the penetration-enhancing concentration of vitamin E may be provided in a variety of forms including semi-solid (gel, paste, cream, lotion, ointment, etc.), liquid, suspension, film or laminate.

7 Claims, No Drawings

PENETRATION ENHANCEMENT OF TOPICALLY APPLIED THERAPEUTIC FORMULATIONS

This is a division of application Ser. No. 07/785,426, filed Oct. 23, 1991 and now abandoned.

BACKGROUND OF THE INVENTION

Due to the easy access, large surface area, application dynamics and the non-invasive nature of the treatment, continuous topical administration has been considered to be a superior mode of drug delivery regardless of whether the bioavailability desired is systemic or dermal, regional or localized. Topical drug delivery provides many advantages over other methods of drug delivery, including the ability to bypass the hepatic "first-pass" elimination and metabolism, elimination of gastrointestinal tract irritation, avoidance of the variation in rates of absorption associated with orally administered drugs and the ability to treat conditions which are local in nature both locally and systemically using the same delivery regimen.

A major challenge in developing topical drug delivery systems has been achieving drug absorption in a reproducible manner and in sufficient quantities to exert a therapeutic effect. The absorption rate of topically applied drugs is generally much slower than that through the gastrointestinal tract. In order to overcome the low bioavailability, improved delivery of drugs has been the subject of worldwide pharmaceutical research for many years. Much of the recent research has focused on methods for enhancing the absorption or penetration of drugs.

Chemical methods of enhancing topical absorption of drugs have received considerable attention and efforts in recent years. Some examples of amphoteric molecules that have been investigated for their penetration-enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V.60, pp. 263–69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," *Pharmacology of the Skin, Advances In Bioloncy of Skin,* (Appleton-Century Craft) V. 12, pp. 257–69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," *Surfactant Science Series,* V. 16, Reiger, M. M. ed. (Marcel Dekker, Inc.) pp. 195–210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (Herschler, U.S. Pat. Nos. 3,740,420 and 3,743,727, and Sandbourn, U.S. Pat. No. 4,575,515), and nitroglycerine (Leslie et. al., U.S. Pat. No. 4,322,433) are a few examples of compounds which have shown an ability to enhance the absorption of various compounds. Also, combinations of enhancers (co-solvent and amphoteric compounds) have been claimed to enhance penetration in some patents (Saito et. al., U.S. Pat. No. 4,590,190 and Cooper et. al., U.S. Pat. Nos. 4,537,776 and 4,552,872). However, since they penetrate the skin, there are serious questions regarding their toxicity and irritation during chronic use.

Since its discovery in the 1920's, vitamin E has been the subject of heated controversy and extensive research. Over the past 25 years there have been a large volume of studies which provide impressive evidence of the need for vitamin E in maintaining normal body metabolism and in the prevention of deficiency diseases.

The most specific biochemical function of vitamin E is as an in vivo anti-oxidant, protecting cell membranes from the damaging effects of free radicals. Vitamin E has also been shown to protect animals against the damaging effects of nitrogen dioxide and ozone, major air pollutants known to lead to free radical formation in the body. Vitamin E has been found to be effective against the toxic effects of mercury, lead and drugs such as adriamycin and nitrofurantoin, to enhance antibody formation, chemotaxis and phagocytosis of polymorphonuclear leukocytes. The effects of vitamin E on cancer are also being evaluated.

In topical applications, most claims for vitamin E have been as a natural moisturizer to relieve dry skin and indirectly to aid in the concealment of wrinkles and facial lines perceived as characteristics of aging. However, other effects for topically applied vitamin E have been the subject of extensive studies. In the treatment of chronic skin diseases (Nikolowski, W., "Vitamin E Dermatology," *Vitamins,* No. 3, 1973), reduction in erythema and swelling (Kamimara, M., "Anti-Inflammatory Activity of Vitamin E," J. Vitaminol., V. 18, pp. 201–09, 1972) and wound healing (Ehrlich, M., Traver, H. and Hunt, T., "Inhibitory Effects of Vitamin E in Collagen Synthesis and Wound Repair," Ann. of Surgery, V. 175 (2), Feb. 1972), vitamin E's therapeutic value has been noted.

Vitamin E'S use in cosmetics has also gone well beyond mere moisturization. Although vitamin E has no sun protection factor to speak of, it does provide protection from ultra violet light by scavenging any free radicals generated by the skin during exposure, thereby suggesting a strong rationale for incorporating the vitamin into suncare preparations. Vitamin E also prevents the formation of nitrosamines, which can be formed from nitrite contaminants present in cosmetics containing amines or amides (Mergens, W. and DeRiter, E., "Nitrosamines in Cosmetics," Cos. Tech., Jan. 1980 and Dunnett, P. C. and Telling, G. M., "Study on the Fate of Bronopol and the Effects of Anti-Oxidants on Nitrosamine Formation in Shampoos and Skin Creams," Int. J. Cos. Sci., V. 6, pp. 241–47, 1984.)

Topical use of drugs and cosmetics containing vitamin E poses little risk. Examination of the literature reveals that vitamin E is widely prescribed in dosages ranging from 200 to 2,000 IU for oral use (Bieri, J. G. et. al., "Medical Uses of Vitamin E," N. Engl. J. Med., V. 308, pp. 1063–71, 1983).

Despite the considerable body of research on vitamin E, there has been no appreciation of its potential to enhance the effects of cosmetic and/or pharmaceutically-active agents.

SUMMARY OF THE INVENTION

The present invention relates to improved compositions and methods for the topical delivery of cosmetic and/or pharmaceutically-active agents to human and animal tissue and systems. The invention is based on the use of cosmetic and/or pharmaceutically-active agent(s) dissolved or dispersed in a vehicle which can be applied topically; said vehicle containing a penetration-enhancing concentration of vitamin E. Combinations with other penetration enhancers may also be employed. In typical practice, the penetration-enhancing concentration of vitamin E can range from about 0.01 to about 20 percent by weight of the composition. However, Vitamin E itself can also serve as both the vehicle and penetration enhancer for the cosmetically- or pharmaceutically-active agent.

The pharmaceutically-active agent may be a medicinal agent such as an agent for treating a cardiovascular condition, an internal condition, a mental health condition, an antibiotic, a protein, a peptide, an anti-inflammatory agent, a chemotherapeutic agent or the like. Cosmetic treating agents such as a sun screen, skin softening agent, acne treating agent, nutritional agent or the like can also be used. The topical compositions containing the penetration-enhancing concentration of vitamin E described in this invention can be provided in a variety of forms including, but not limited to, semi-solid (gel, paste, ointment, cream, lotion, etc.), liquid, suspension, film or laminate.

DESCRIPTION OF THE INVENTION

Topical application of the compositions described herein implies that the composition is spread or laid upon epidermal tissue especially outer skin or membrane, including the skin, membrane or mucosal tissues of the oral, nasal, anal and vaginal cavities. This invention further describes the use of safe and effective quantities of cosmetically or pharmaceutically-active agents in a topically applied composition containing a penetration-enhancing concentration of vitamin E. The term "safe and effective" is meant to imply a sufficient amount of composition to provide the desired systemic and/or local effect, without undue toxicity, irritation, allergic response, and the like, commensurate with a reasonable benefit/risk ratio.

The compositions of this invention require at least a cosmetically or pharmaceutically-active agent in a suitable vehicle containing a penetration-enhancing concentration of vitamin E. Vitamin E can also serve as both the vehicle and penetration enhancer for the cosmetically or pharmaceutically active agent. The compositions described in this invention may additionally contain other optimal ingredients which may improve their cosmetic appeal or acceptability, including, but not limited to, thickeners, pigments, flavors, fragrances, sweeteners, preservatives, opacifiers, hydrophobic agents, fillers, glycerin, propylene glycol, polyethylene glycol, buffers and other pharmaceutical necessities.

The compositions described in this invention may also contain mucosally tenacious polymeric agents when applying the compositions topically in the oral, nasal, anal or vaginal cavities. Among such mucosally tenacious polymeric agents which could be utilized in the compositions described by this invention are agar, algin, carageenan, fucoidan, laminoran, furcellaran, gum arabic ghatti, gum karaya, gum tragacanth, guar gum, locust bean gum, quince seed gum, psyllium seed gum, flax seed gum, okra gum, tamarind seed gum, pectin, xanthan gum, various dextrans, chemically modified cellulose polymers, polyvinyl alcohol, polyvinyl pyrrolidone, polyacrylic acid derivatives with/without other monomers to form various copolymers, polyacrylamide, ethylene oxide polymers, polyethylenimines, gelatin and the like. The various polymeric materials herein described are illustrative of the many agents from which a composition of this invention can be compounded into useful mucosally tenacious vehicles. They may be used singly or in combination, in a wide range of concentrations and in the presence of many other agents intended to control rates of water absorption and swelling. The preferred concentration is from about 0.1 to 30 percent of the composition by weight and most preferably about 0.5 to 15 percent.

The cosmetically or pharmaceutically-active agents useful in accordance with this invention may be selected generally from the class of medicinal agents and cosmetic agents. Such agents include, but are not limited to, agents for treating internal conditions such as blood glucose regulators, tolbutamide (anti-diabetic), levothyroxine (thyroid conditions), propantheline (anti-spasmotic), cimetidine (antacid), phenylpropanolamine (anti-obesity), atropine or diphenoxylate (anti-diarrheal agents), docusate (laxative) or prochlorperazine (anti-nauseant); anti-microbials including sulfonamides, sulfones and natural and synthetic antibacterial agents; antibiotics, anti-myobacterial agents, anti-malarials, anti-amebic agents, agents active against protozoan diseases, anti-fungal agents or anti-viral agents; agents for the treatment of cardiovascular conditions such as chlorothiazide (diuretic), propanolol (anti-hypertensive), hydralazine (peripheral vasodilator), nitroglycerin (coronary vasodilator), metoprolol (beta-blocker), procainamide (anti-arrythmic), clofibrate (cholesterol reducer) or coumadin (anti-coagulant); male and female sex hormones and their analogues, peptide and protein hormones; non-steroidal and steroidal anti-inflammatory agents such as acetaminophen, phenacetin, aspirin, hydrocortisone, ibuprofen, ketoprofen, flurbiprofen, naproxen or fenoprofen; anti-histamines such as diphenyldramine hydrochloride; chemotherapeutic agents such as sulfathiazole, doxorubicin, cisplatin or nitrofurazone; agents for treating mental health such as haloperidol or chlorpromazine (tranquilizers), doxepin (psycho-stimulant), phenyotoin (anti-convulsant), levodopa (anti-parkinson), benzodiazepine (anti-anxiety) or phenobarbital (sedative); topical anesthetics or analgesics such as benzocaine or lidocaine; cardiac tonics; birth control agents such as estrogen; ophthalmic treating agents such as trimolol or gentamycin; anti-titussives or expectorants such as codeine phosphate or dextromethorphin; oral antiseptics such as chlorhexidine gluconate, hexylresorcinol or cetylpyridinium chloride; enzymes such as dextranase; bone active agents such as organodiphosphonates; anti-arthritics; anti-ulcer drugs; skeletal and smooth muscle relaxants; prostaglandins. Cosmetic agents include sun screens such as p-dimethylaminobenzoic acid; skin softeners such as urea; keratolytic agents such as salicylic acid; acne agents such as benzoyl peroxide, perfumes and the like. Nutritional agents such as vitamins or minerals like iron or riboflavin may also be useful treating agents. This list should not be considered limiting in that other agents could be used by those skilled in the art without departing from the teachings of this invention. The cosmetically or pharmaceutically-active agent may be used singly or in combination with additional such agents.

The cosmetically or pharmaceutically-active agent(s) can be used at any safe and effective level. In the preferred embodiments, the composition described in the present invention contains about 0.01 to 10 percent of the cosmetically or pharmaceutically-active agent, by weight of the composition. However, it will be appreciated that effective amounts of medicinal agents vary with the particular agent employed, the condition being treated and the biological half-life of the agent, as well as varying with the type and weight of the animal to be treated. Consequently, effective amounts of cosmetically or pharmaceutically-active agents cannot be specified for each agent. An effective amount is that which in a composition provides a sufficient amount of treating agent to provide the desired systemic or local therapeutic effect, for the desired period of time.

The enhancing agent of the invention is vitamin E. The preferred concentration of the vitamin E is about 0.01 to 20 percent by weight of the composition and most preferably about 0.1 to 15 percent, however, depending on the nature of the delivery system or vehicle, any concentration demonstrating a penetration-enhancing effect for a cosmetically or pharmaceutically-active agent may be used. Vitamin E can be in the form of the free alcohol, acetate, linoleate, nicotinate or acid succinate esters. Other compounds and isomeric forms of vitamin E can also be used to enhance the penetration of cosmetically or pharmaceutically-active agents. The penetration-enhancing vitamin E may be used singly, or in combination with other penetration-enhancing agents without departing from the teachings of this invention.

In addition to the components mentioned above, the semi-solid compositions of this invention may also contain a pharmaceutically and/or cosmetically acceptable solvent. The solvent should be selected so as not to interfere with the penetration-enhancing action of the vitamin E. Preferred solvents include, but are not limited to, water, glycerin, mineral oil, propylene glycol, triacetin, sorbitol solution, ethanol, liquid petrolatum, or polyethylene glycols. Such solvents may comprise from about 5 to 95 percent, preferably about 20 to 90 percent, of the total composition by weight. The compositions described in the invention may also contain synthetic or natural elastomeric substances or hydrophilic plasticizer resins which will give the topical composition a cohesive nature in order to keep the application in contact with the exposed application area for extended periods of time. Examples of preferred materials include, but are not limited to, polyvinylacetate, polyisobutylene, polyvinyl alcohol, petrolatum wax, polyethylene, butadiene-styrene, paraffin, isobutylene-isopyrene, chicle, balata, sorva, gutta percha, lechi caspi or jelutons. These materials may comprise from about 0.1 to 60 percent, preferably about 1 to 40 percent, of the total composition by weight.

The compositions described in the present invention may also contain other formulative adjuvants conventionally found in cosmetic and pharmaceutical compositions at levels which are familiar to those skilled in the art. Such ingredients include, but are not limited to, excipients, dyes, perfumes, flavors, fragrances, opacifiers, thickening agents, mucosally tenacious polymers, preservatives, anti-oxidants, gelling agents, surfactants and stabilizers. Such materials when added should be selected so as not to interfere with the penetration-enhancement provided by the vitamin E.

The dosage of topical application should be selected based on the specific condition or conditions being treated when using compositions described in the present invention. One regimen of topical treatment described in the present invention involves applying the composition directly to the skin. The composition may also be applied to the oral, anal, nasal or vaginal cavity. The rate and quantity of application and duration of treatment will depend upon the condition being treated, its progress and response, the desired effect, severity of the condition, surface area being treated and other factors evident to those skilled in the art of medical judgment.

The compositions are usually applied once to about six times daily, depending on the cosmetically or pharmaceutically-active agent and the condition being treated. However, any safe and effective regimen can be employed.

The following non-limiting examples are illustrative of the types of compositions containing penetration-enhancing concentrations of vitamin E which can be used in accordance with the teachings of this invention.

EXAMPLE 1

A composition of matter is prepared in accordance with the following formula and directions:

| | |
|---|---|
| Vitamin E | 5.0% |
| Hydrocortisone | 2.0% |
| Sorbitol Solution | 60.0% |
| Sodium Carboxymethylcellulose | 1.4% |
| Glycerin | 29.4% |
| Fumed Silica | 2.0% |
| Preservative | 0.1% |
| Titanium Dioxide | 0.1% |

Intimately mix the hydrocortisone, preservative and titanium dioxide in the sorbitol solution with a mechanical mixer. Add fumed silica and vitamin E and mix well. In a separate container carefully disperse sodium carboxymethylcellulose in the glycerin. Add this mix to the sorbitol dispersion and mix under vacuum for twenty minutes. The resulting cream should be smooth and uniform, suitable for topical application.

EXAMPLE 2

| | |
|---|---|
| Vitamin E | 3.0% |
| Estradiol | 4.5% |
| Polyvinyl Acetate | 43.5% |
| Triacetin | 21.4% |
| Ethanol | 21.4% |
| Triethanolamine | 1.0% |
| Fumed Silica | 5.0 |
| Titanium Dioxide | 0.1% |
| Preservative | 0.1% |

Dissolve the polyvinyl acetate in triacetin with the aid of heat. Cool slowly. Add ethanol. With the aid of a Tekmar Mixer add triethanolamine, titanium dioxide and preservative. Add to this mixture while mixing fumed silica, estradiol and vitamin E. Mix under vacuum for about twenty minutes. The resulting cream, which is suitable for topical use, should be smooth and uniform.

EXAMPLE 3

| | |
|---|---|
| Vitamin E | 10.0% |
| Ketoprofen | 1.0% |
| Polyisobutylene | 15.0% |
| Mineral Oil | 69.5% |
| Triethanolamine | 1.0% |
| Flavor | 0.2% |
| Preservative | 0.1% |
| Fumed Silica | 3.0% |
| Sweetener | 0.2% |

Dissolve the polyisobutylene in mineral oil with the aid of heat. If desired, a pre-mix of polyisobutylene/mineral oil may be prepared and used for several batches. Cool the batch slowly. Add flavor, sweetener and preservative and mix with a Tekmar Mixer at moderate speed. Add fumed silica with mixing. Add triethanolamine, vitamin E and ketoprofen. Mix well with vacuum for twenty minutes. The resulting composition is a smooth, homogeneous cream with a pleasant taste, suitable for application in the oral cavity.

For improved mucosal tenacity in the oral, nasal, anal and vaginal cavities, the addition of mucosally tenacious polymers are recommended as in the following example.

EXAMPLE 4

| | |
|---|---|
| Vitamin E | 14.0% |
| Nystatin | 0.5% |
| Polyvinyl Acetate | 37.2% |
| Triacetin | 40.9% |
| Fumed Silica | 2.0% |
| Triethanolamine | 0.6% |
| Preservative | 0.1% |
| Sodium Carboxymethylcellulose | 1.6% |
| Polyethylene Oxide | 3.0% |
| Titanium Dioxide | 0.1% |

Dissolve polyvinyl acetate in triacetin with the aid of heat. Cool slowly. With the aid of a Tekmar Mixer add triethanolamine, titanium dioxide and preservative. Add fumed silica while mixing. Slowly add sodium carboxymethylcellulose and polyethylene oxide allowing for about five minutes of mixing between additions of these polymers. Add nystatin and vitamin E and mix under vacuum for about twenty minutes. The composition which results is a smooth, uniform cream which is suitable for use in the vaginal cavity for the treatment of fungal or yeast infection.

Another useful composition is a mucosally-tenacious film prepared in accordance with the following formula:

EXAMPLE 5

| | |
|---|---|
| Vitamin E | 1.5% |
| Ibuprofen | 0.5% |
| Ethylene Oxide Homopolymer (3,000,000 MW) | 30.0% |
| Polyvinyl pyrrolidone | 51.0% |
| Polyethylene Glycol 4000 | 15.0% |
| Glycerin | 2.0% |

The ethylene oxide homopolymer, polyvinyl pyrrolidone, polyethylene glycol and glycerin are comminuted into an intimate mixture and warmed to 40° C., at which time the ibuprofen and vitamin E are incorporated and mixed thoroughly. The mixture is cooled to about 25° C. and then extruded through stainless steel rollers into a film approximately 2 mm thick. After further cooling, the extruded film is cut by knives into rectangular strips. In order to use, the strips are moistened with water and pressed firmly on the mucosal tissue.

EXAMPLE 6

Yet another example of a useful embodiment of this invention is the combination of a cosmetically or pharmaceutically-active agent with a penetration-enhancing concentration of vitamin E incorporated into vesicles or liposomes like those described by Baldeschwieler et. al. in U.S. Pat. No. 4,310,505. The agents can be incorporated into the vesicles described in U.S. Pat. No. 4,310,505 by sonicating the vesicles and then adding vitamin E and flurbiprofen, as an example of a pharmaceutically-active agent. This procedure is more fully described by Huang, et. al. Biochem., V. 18 p. 1702–07 (1979).

EXAMPLE 7

| | |
|---|---|
| Vitamin E Acetate | 0.6% |
| Purified Water | 80.4% |
| Polyacrylic Acid | 2.0% |
| Ketoprofen | 1.0% |
| Sweetener | 0.3% |
| Preservative | 0.1% |
| Pluronic F127 (70/30 polyoxyethylene-polyoxypropylene block copolymer, MW 12,700) | 15.0% |
| Sodium Hydroxide | 0.6% |

Disperse polyacrylic acid in the purified water using a Tekmar Mixer at high speed until no lumps are evident. Add Pluronic F127 and mix at low speed for five (5) minutes. Heat the mixing vessel to 45° C. and add the ketoprofen until dissolved (about two (2) minutes) with the Tekmar Mixer. Cool the vessel to 25° C. Add preservative, sweetener, vitamin E acetate and sodium hydroxide. Mix under vacuum for ten minutes. The resulting product is a smooth homogeneous gel.

EXAMPLE 8

The following penetration studies examine the penetration-enhancing effects imparted to the compositions described in this invention by vitamin E. When vitamin E is present in the compositions described in this invention, penetration is enhanced when compared to similar compositions which do not contain vitamin E.

The penetration studies were carried out in the following manner. Porcine esophageal tissue (muscle removed with surgical scissors) was used in the studies completed, using the Bronaugh flow-through diffusion cell system (Crown Glass Company, Somerville, N.J.). The flow-through cells were machined from Teflon to enable the fashioning of a small receptor. A circle of tissue, mucosal side up, is placed on the ledge of the receptor, and the top is screwed tightly into place. The inside section of the top is free to rotate so that the top can be tightened without twisting or tearing the tissue. The exposed tissue area is 7 $mm^2$ (diameter about 3 mm.). The tube for each sidearm falls 1 mm. short of reaching the inside receptor wall. The receptor solution, therefore, enters and leaves the receptor through a hole that is the size of the receptor. A glass plug forms the bottom of the receptor so that the inside contents are visible, permitting verification that air bubbles are not present in the receptor. The temperature of the diffusion cells is maintained at 37° C. by heated aluminum holding blocks. Temperature controlled water is pumped through the blocks using a heating circulator. A multi-channel peristaltic cassette pump controls the flow rate of receptor fluid to each cell. The effluent is collected in scintillation vials held in a fraction collector. A receptor flow rate of 2 cc./hr. was selected based on previously published data (Bronough, R. L. and Stewart, R. F., "Methods for In Vitro Percutaneous Absorption Studies IV: The Flow-Through Diffusion Cell," J. Pharm. Sci. V. 74, pp. 64–67, 1985). Phosphate buffered saline (pH 7.4) was used as the receptor solution in all experiments.

Compositions for these experiments were prepared with radio-labeled pharmaceutically-active agents and a known quantity was applied in a controlled manner to the exposed surface of the tissue in the diffusion cells. Receptor solution was collected over preset time intervals for up to 24 hours. The cells were covered with Parafilm to prevent evaporation. The amount of pharmaceutically-active agent penetrating through the tissue was determined by measuring the radioactivity in the scintillation vials with a liquid scintillation counter (Beckman).

The permeability coefficient (Kp) is calculated by dividing the net total transfer of permeant (radioisotope) during each time interval by the quantity of permeant remaining on the donor side of the tissue and the area of the membrane exposed for diffusion (cell constant). Kp was calculated from values obtained after a steady-state was reached. This was estimated graphically and confirmed by comparing $K_p$ calculated at various time intervals. Seeing no general time trend, it was concluded that the measurements were taken during steady-state flux. The following equation is used to calculate $K_p$:

$$K_p = \frac{Q}{A \cdot T \cdot (C_o - C_i)}$$

Where:
$K_p$=Permeability Coefficient (cm./min.)
Q=Quantity of Compound Transversing the Tissue (ugm.)
A=Area of Exposure (cm.$^2$)
T=Time of Exposure (min.)
$C_O$=Concentration on the Outer (Donor) Side of the Tissue (ugm./ml.)
$C_i$=Concentration on the Inner (Receptor) Side of the Tissue (ugm./ml.)

Determinations of $K_p$ were done in triplicate at minimum to yield an average $K_p$ value.

|  | A (% w/w) | B (% ww) |
| --- | --- | --- |
| Vitamin E | — | 4.0 |
| Polyisobutylene | 15.0 | 15.0 |
| Mineral Oil | 80.6 | 76.6 |
| Ketoprofen | 0.5 | 0.5 |
| Preservative | 0.1 | 0.1 |
| Fumed Silica | 2.9 | 2.9 |
| Flavor | 0.2 | 0.2 |
| Sweetener | 0.2 | 0.2 |
| Titanium Dioxide | 0.1 | 0.1 |
| Triethanolamine | 0.4 | 0.4 |
| pH | 5.6 | 5.7 |
| $K_p$ (cm./min. × $10^{-6}$) | 14.5 | 19.9 |

The Example 8 study was repeated with five other formulations as detailed in Examples 9 through 13.

EXAMPLE 9

|  | C (% w/w) | D (% w/w) | E (% w/w) |
| --- | --- | --- | --- |
| Vitamin E | — | 3.0 | 5.0 |
| Polyisobutylene | 15.0 | 15.0 | 15.0 |
| Mineral Oil | 79.9 | 76.8 | 74.8 |
| Ketoprofen | 1.0 | 1.0 | 1.0 |
| Flavor | 0.2 | 0.2 | 0.2 |
| Preservative | 0.1 | 0.1 | 0.1 |
| Fumed Silica | 2.9 | 2.9 | 2.9 |
| Sweetener | 0.2 | 0.2 | 0.2 |
| Titanium Dioxide | 0.1 | 0.1 | 0.1 |
| Triethanolamine | 0.6 | 0.7 | 0.7 |
| pH | 5.5 | 5.5 | 5.4 |
| $K_p$ (cm./min. × $10^{-6}$) | 13.9 | 31.3 | 38.8 |

As can be easily seen in the examples 7 and 8, the vitamin E is contributing a significant penetration-enhancement of ketoprofen, to the point where the penetration rate of 0.5 percent ketoprofen in the presence of vitamin E is greater than that of 1.0 percent ketoprofen without vitamin E. A practical significance of these results lies in the fact that lower doses of pharmaceutically-active agents may be used in the compositions described in this invention, and thereby the potential exists for reducing negative side effects associated with the pharmaceutically-active agent.

EXAMPLE 10

|  | F | G |
| --- | --- | --- |
| Vitamin E | — | 5.0 |
| Polyvinyl acetate | 57.2 | 54.2 |
| Triacetin | 19.1 | 18.1 |
| Ethanol | 19.1 | 18.1 |
| Ketoprofen | 1.0 | 1.0 |
| Preservative | 0.1 | 0.1 |
| Triethanolamine | 0.5 | 0.5 |
| Fumed Silica | 3.0 | 3.0 |
| pH | 5.9 | 5.9 |
| $K_p$ (cm./min. × $10^{-6}$) | 11.8 | 16.5 |

EXAMPLE 11

|  | H (% w/w) | I (% w/w) |
| --- | --- | --- |
| Vitamin E | — | 3.50 |
| Polyisobutylene | 15.00 | 15.00 |
| Mineral Oil | 74.65 | 71.20 |
| Fumed Silica | 2.00 | 2.00 |
| Estradiol | 3.50 | 3.50 |
| Preservative | 0.10 | 0.10 |
| Sodium carboxymethylcellulose | 1.60 | 1.60 |
| Polyethylene Oxide | 3.00 | 3.00 |
| Titanium Dioxide | 0.10 | 0.10 |
| Triethanolamine | 0.05 | — |
| pH | 6.1 | 6.2 |
| $K_p$ (cm./min. × $10^{-6}$) | 5.6 | 7.3 |

EXAMPLE 12

|  | J (% w/w) | K (% w/w) |
| --- | --- | --- |
| Vitamin E | — | 3.0 |
| Estradiol | 1.5 | 1.5 |
| Sorbitol Solution | 64.8 | 61.8 |
| Glycerin | 29.4 | 29.4 |
| Sodium Carboxymethylcellulose | 1.6 | 1.6 |
| Fumed Silica | 2.5 | 2.5 |
| Preservative | 0.1 | 0.1 |
| Titanium Dioxide | 0.1 | 0.1 |
| pH | 6.5 | 6.4 |
| $K_p$ (cm./min. × $10^{-6}$) | 5.1 | 7.3 |

EXAMPLE 13

|  | L (% w/w) | M (% w/w) |
| --- | --- | --- |
| Ketoprofen | 1.0 | 1.0 |
| Vitamin E Acetate | 0.3 | — |
| Purified Water | 80.7 | 81.0 |
| Polyacrylic Acid | 2.0 | 2.0 |
| Sweetener | 0.3 | 0.3 |
| Preservative | 0.1 | 0.1 |
| Pluronic F127 | 15.0 | 15.0 |

-continued

|  | L (% w/w) | M (% w/w) |
|---|---|---|
| Sodium Hydroxide | 0.6 | 0.5 |
| pH | 5.7 | 5.7 |
| $K_p$ (cm./min. × $10^{-6}$) | 48.3 | 34.3 |

The previous examples, which should not be considered limiting, clearly demonstrate the penetration-enhancement which vitamin E provides to topically applied products containing cosmetically or pharmaceutically-active agents.

Further changes and modifications of the compositions described in this invention may be made by those skilled in the art, without departing from the teaching of this invention.

What is claimed is:

1. A method of enhancing the penetration of a therapeutic agent, wherein the method consists of the following steps performed sequentially:

A) combining 0.01–10 weight percent of said therapeutic agent other than vitamin E with a composition consisting essentially of (i) 0.01–20 weight percent vitamin E as the penetration enhancing agent; (ii) 5–95 wt. percent solvent selected from the group consisting of mineral oil, water, ethanol, triacetin, glycerin and propylene glycol; (iii) a cohesion agent selected from the group consisting of polyisobutylene, polyvinyl acetate and polyvinyl alcohol, and (iv) a thickening agent; and B) applying said composition topically to a subject.

2. The method of claim 1 in which the therapeutically-active agent is a pharmaceutically-active agent and is about 0.01 to 10% of the composition.

3. The method of claim 2 in which the said composition is in the form selected from the group consisting of a gel, paste, ointment, cream, lotion, liquid suspension, suppository, film and laminate.

4. The method according to claim 1 in which said composition includes a pharmaceutically acceptable thickening agent.

5. The method according to claim 4 in which the thickening agent is a block copolymer of polyoxyethylene and polyoxypropylene.

6. The method according to claim 5 in which the composition contains water, and the thickening agent is hydroxypropyl cellulose and the composition contains propylene glycol as a solvent.

7. The method according to claim 1 in which the therapeutically-active agent is a cosmetically-active agent and is about 0.01 to 10% of the composition.

* * * * *